United States Patent [19]
Murdoch et al.

[11] Patent Number: 6,142,631
[45] Date of Patent: Nov. 7, 2000

[54] REDUCED LOGMAR VISUAL ACUITY TEST CHART

[75] Inventors: Ian E. Murdoch, Bucks; D. Allstair H. Laidlaw, London; Dan A. Rosser, Highgate; Fred W. Fitzke, London, all of United Kingdom

[73] Assignees: University College London; Moorfields Eye Hospital NHS Trust, both of London, United Kingdom

[21] Appl. No.: 09/235,279

[22] Filed: Jan. 22, 1999

[51] Int. Cl.$^7$ ...................................................... A61B 3/00
[52] U.S. Cl. ............................................................ 351/239
[58] Field of Search ................................... 351/201, 209, 351/239, 240, 244, 243, 242, 246, 237

[56] References Cited

U.S. PATENT DOCUMENTS

| | | | |
|---|---|---|---|
| 4,968,131 | 11/1990 | Lewis | 351/239 |
| 5,121,981 | 6/1992 | Waltuck et al. | |
| 5,129,720 | 7/1992 | Jovicevic | 351/243 |
| 5,416,540 | 5/1995 | Hayashi | |
| 5,568,209 | 10/1996 | Priester et al. | 351/243 |

FOREIGN PATENT DOCUMENTS 2 267 159   11/1993   United Kingdom .

OTHER PUBLICATIONS

Bailey et al, "New Design Principles for Visual Acuity Letter Charts," Amer. Journal of Optometry & Physiological Optics, vol. 53, No. 11, pp. 740–745 (1976).

McGraw et al, "Measurement of letter acuity in preschool children," Ophthal. Physiol. Opt., vol. 15, Suppl. 1, pp. S11–S17 (1995).

McGraw et al, "Glasgow Acuity Cards: a new test for the measurement of letter acuity in children," Ophthal. Physiol. Opt., vol. 13, pp. 400–404 (1993).

Ferris, III et al, "New Visual Acuity Charts for Clinical Research," Amer. Journal of Ophthalmology, vol. 94, pp. 91–96 (1982).

Ferris, III et al, "Standardized Illumination for Visual Acuity Testing in Clinical Research," Amer. Journal of Ophthalmology, vol. 94, pp. 97–98 (1982).

Primary Examiner—George Manuel
Attorney, Agent, or Firm—Nixon & Vanderhye

[57] ABSTRACT

An improved visual acuity chart is disclosed. The ratio of the size of the optotypes of neighbouring lines on the chart is a constant and preferably the size decrement between lines is 0.1 logMAR. Each line of optotypes has two, three or four optotypes, preferably three. Crowding bars for visual acuity charts are also disclosed. These bars are spaced from the ends of row and/or above and below the top and bottom lines. The individual bars may be joined together with linking sections. The spacing form the optotypes is preferably one half the width or height of the optotypes and their breadth is preferably that of the strokes of the optotypes.

20 Claims, 2 Drawing Sheets

REDUCED LOGMAR VISUAL ACUITY TEST CHART

FIELD OF THE INVENTION

The present invention relates to eye-charts used for measuring the visual acuity of a subject as may be done in a research setting or in a clinical setting for example in a hospital or before the purchase of spectacles or contact lenses.

BACKGROUND TO THE INVENTION

The Snellen acuity chart is the most widely used form of chart used in clinical practice. In a test the subject is asked to read the lines of letters, each line of which is progressively smaller down the chart, to find the smallest that can be read. This chart has inherent design flaws which result in imprecise and poorly repeatable measurements. Among these flaws ones related to "crowding"—the environment of neighbours surrounding a letter—varying legibility of the particular letters employed and the non-uniform scale of letter sizes used (as opposed to the uniform logarithmic scale appropriate to acuity measurement). These flaws and the non-uniform Snellen fraction measurement scale render acuity data difficult to analyse and the test insensitive to changes over time in a subject's acuity.

The form of visual acuity chart preferred for research is the ETDRS logMAR chart. The ETDRS chart is named after the "Early Treatment Diabetic Retinopathy Study" for which it was originally produced. This chart has fourteen lines of five letters each. In this chart the logarithm to base 10 of the size of the letters in each line reduces by 0.1 (which is a reduction in size by a factor of approximately 1.259). This chart addresses the problems of the Snellen chart stated above, the ETDRS chart providing precise repeatable measurements and readily analysable decimalised acuity data. This ETDRS chart is, however, considered widely too cumbersome for routine clinical use and has not been adopted for such use.

SUMMARY OF THE INVENTION

According a first aspect of the present invention there is provided a visual acuity chart having a plurality of lines of optotypes, wherein the ratio of the size of the optotypes of each line of the plurality to the size of the optotypes of preceding line is a constant, and wherein each line of the plurality has between two and four optotypes.

The ratio between the sizes of optotypes of neighbouring lines being a constant is mathematically equivalent to the difference in the logarithm of the size of the optotypes of a line differing from that of the next by a constant.

Each line of the plurality preferably has three optotypes, but may have two or four.

The said ratio may be such that the difference between the logarithm to base 10 of the size of the optotypes of each line of the plurality and the logarithm to base 10 of the size of those of the next: is 0.1.

The said optotypes may be drawn from the Sloan set.

The said visual acuity chart may have at least one crowding bar spaced from the end of one of the said lines of optotypes or spaced above the top line of optotypes or below the bottom line of optotypes.

Two such crowding bars may be joined by linking sections.

A said crowding bar may be spaced from the end of a row by half the width of the optotypes of that row or may be spaced above the top line of optotypes or below the bottom line of optotypes by half the height of the optotypes of the top or bottom row respectively.

The breadth of the crowding bar may be equal to the width of the strokes of the optotypes.

According to a second aspect of the invention there is provided a visual acuity chart having a plurality of optotypes, the size of the optotypes of the lines of the plurality decreasing line by line, the said acuity chart having at least one crowding bar spaced from the end of one of the said lines of optotypes or spaced above the top line of optotypes or below the bottom line of optotypes.

The crowding bars may be as stated above in relation to the first aspect of the invention.

According to a third aspect of the invention there is provided a method of testing a subject's visual acuity comprising the subject viewing a visual acuity chart according to either the first or second aspect of the invention above and the subject responding by indicating his or her identification of at least a particular one of the optotypes displayed on the chart.

According to a fourth aspect of the invention there is provided an apparatus for producing an image, viewable by a subject, of a chart according to either of the first or second aspect of the invention.

The said image may be produced on an emissive display, for example, a computer monitor or may be formed by projection onto a screen or into the eye.

BRIEF DESCRIPTION OF THE DRAWINGS

There will now be described by way of example only the preferred embodiment of the invention with reference to the accompanying drawings, of which.

DESCRIPTION OF THE PREFERRED EMBODIMENT

Figure 1:
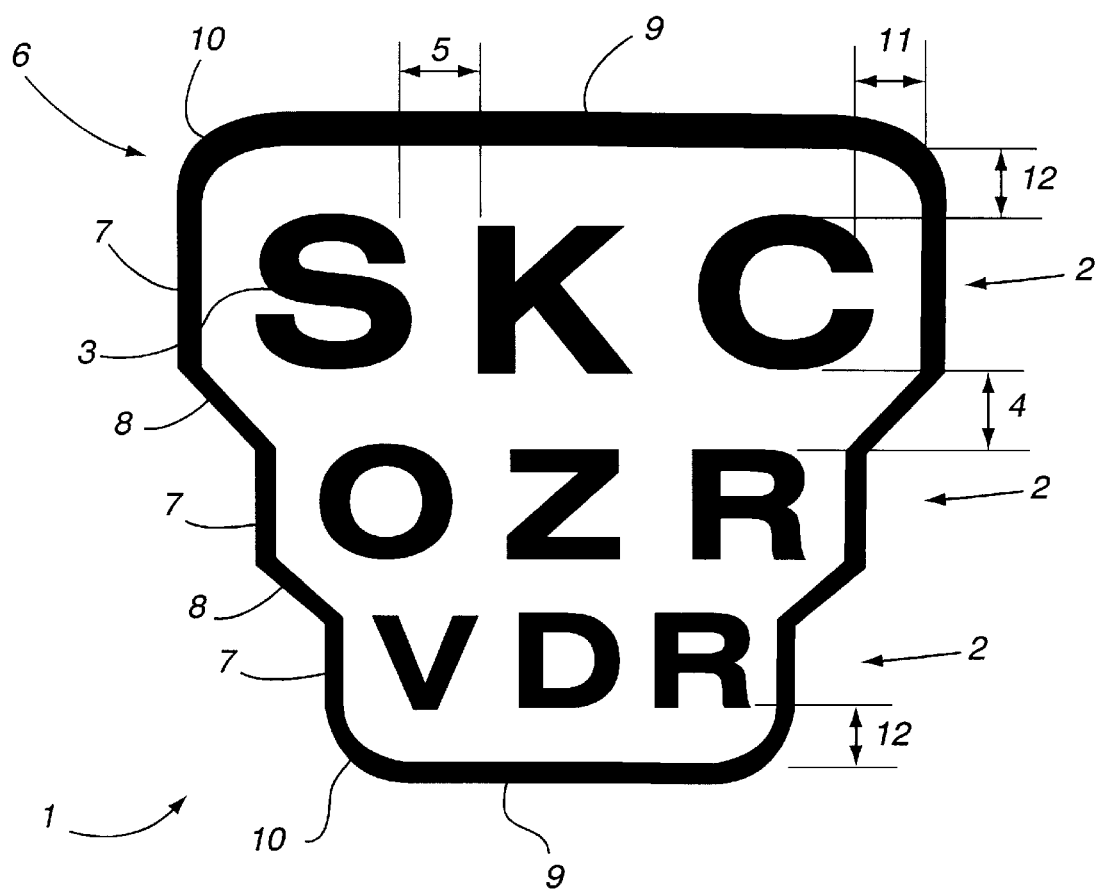
FIG. 1 is a visual acuity chart according to the present invention but has only three rows of optotypes for ease of illustration.

FIG. 1 shows a visual acuity chart 1 according to the present invention- This type of chart is known herein as a "Reduced logMAR" chart for reasons which will become apparent. For ease of illustration FIG. 1 has only three rows 2 of optotypes 3, for example, capital letters. In the preferred embodiment of the chart there are fourteen rows.

Each row 2 of the chart has three optotypes 3, but alternatively two or four optotypes may be used. Each row of the chart is smaller in size, compared to the row above, by the same factor, as is advantageous for repeatable and easily analysable measurements. Preferably the logarithm to base 10 of the size of the optotypes reduces by 0.1 from line to line.

Preferably the optotypes are letters taken from those of the Sloan set. This set of letters, as is known in the art, are chosen to have small differences in legibility. Other sets of optotypes may be used, however, and may be more appropriate for some subjects, for example, the "Illiterate E" and "Landholt C" sets. The Illiterate E set is a capital E orientated in each of four directions separated by 90°. Further the letters for a, line are preferably chosen so that each line has about the same legibility as a whole, for example, a line where all the letters are the more difficult ones of the Sloan set is not chosen.

In the preferred embodiment the letters used are of a Gothic font and fit into a 5 by 5 grid of squares with the strokes of the letters being the width of one square.

Preferably the spacing 4 between two rows is half of the height of the lower row, and preferably the spacing between letters 5 is half the width of the letters.

There is a difference in legibility between optotypes that are surrounded by optotypes on all sides and those that are not, for examples those at the end of a row or those in the top and bottom rows. This phenomenon is known as "crowding". To reduce legibility variations crowding bars 6 are employed. Any combination of bars to the left and/or right of rows and above the top row and/or below the bottom row may be used, but preferably all of those are used. It is also preferred to join the crowding bars 7 at the ends of the rows with linking sections 8 which are tapered if the crowding bars 7 differ in width. It is also preferable to join the crowding bars above the top line or below the bottom line to the crowding bars 7 with further linking sections 10. It is thought that crowding bars while not unhelpful to normal subjects may not be essential to their use of the chart. There are however conditions such a amblopia for which crowding is a significant effect and for which the crowding bars result in better test results.

The preferred widths and positions of the crowding bars are as follows. Crowding bars 7 to the left or right of a row are spaced by a distance 11 from the end of row of half the width of the optotypes of that row and have a width equal to the stroke width of the optotypes of that row. Crowding bars above the top line or below the bottom line are spaced by a distance 12 equal to half the height of the top row or the bottom row respectively and have a height equal three stroke width of the optotypes of the top or bottom row respectively.

The top line of optotypes preferably has a size of 1.0 logMAR. The logMAR unit is the logarithm to base 10 of a subject's minimum angle of resolution. 1.0 logMAR is equivalent to 20/200 in Snellen notation. Since logMAR is a measure of angle the absolute size (for example in millimetres) of the optotypes depends on the distance from which it is intended to be viewed. Preferably this distance is marked on the chart. On a chart having a decrement between lines of 0.1 in the logarithm to base 10 of the size of the optotypes an having a first line of size 1.0 logMAR the second line will have a size of 0.9 logMAR, the third 0.8 logMAR and so on.

Figure 2:
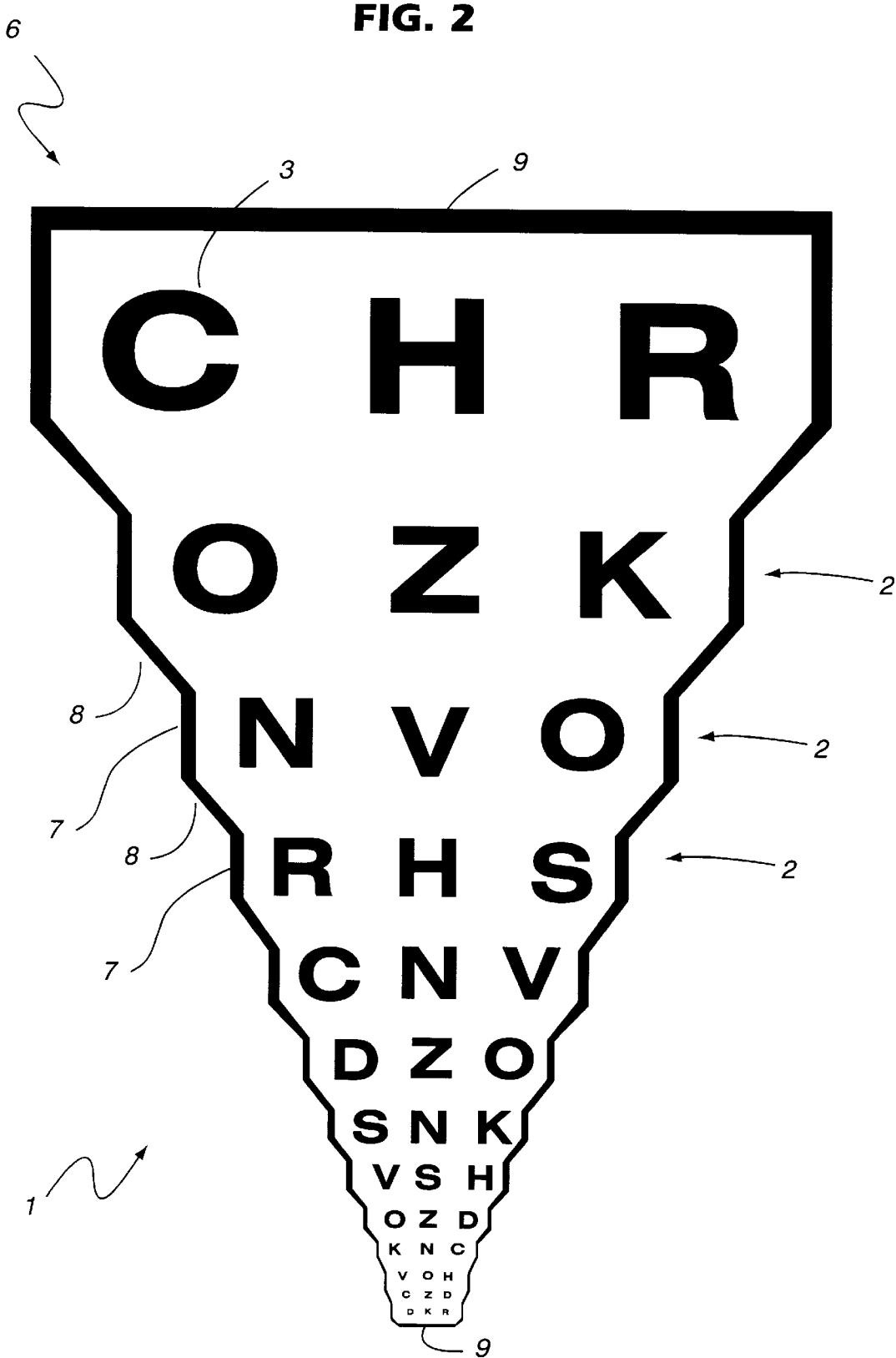
FIG. 2 is a visual acuity chart according to the present invention having thirteen rows of optotypes.

FIG. 2 is a prototype chart according to the present invention. This chart has 13 rows of optotypes with the first being of size 0.9 logMAR (The chart of FIG. 2 has been reduced to fit on the page, the chart that would be used in clinical practice being larger.) The chart of the preferred embodiment has 14 rows having an extra line at the top of the size 1.0 logMAR. FIG. 2 is marked with the same reference numerals as FIG. 1 where appropriate.

The following table gives the actual sizes for the letters of the chart of FIG. 2. Letters for two charts are suggested, since using a chart with one set of letters for testing one eye of a subject and a different chart for testing the other reduces the effect caused by the subject remembering where the letters are. The letters used in the chart of FIG. 2 are those given for chart #1 in TABLE 1. The lower rows of FIG. 2 may be illegible at the reduced scale of reproduction and may be read from table 1. These charts are for viewing at 4 meters with the top line being 0.9 logMAR

TABLE 1

| Line | Letter width (mm) | Stroke width (mm) | Crowding bar separation from row end | Letters for chart #1 | Letters for Chart #2 |
|---|---|---|---|---|---|
| 1 | 46.21 | 9.24 | 23.11 | KNS | CHR |
| 2 | 36.71 | 7.34 | 18.35 | SHV | OZK |
| 3 | 29.16 | 5.83 | 14.58 | DZO | NVO |
| 4 | 23.16 | 4.63 | 11.58 | CNK | RHS |
| 5 | 18.40 | 3.68 | 9.20 | HOV | QNV |
| 6 | 14.61 | 2.92 | 7.31 | CDZ | DZO |
| 7 | 11.61 | 2.32 | 5.80 | OKN | SNK |
| 8 | 9.22 | 1.84 | 4.61 | VHC | VSH |
| 9 | 7.32 | 1.46 | 3.66 | ZSK | OZD |
| 10 | 5.82 | 1.16 | 2.91 | RHO | KNC |
| 11 | 4.62 | 0.92 | 2.31 | KVD | VOH |
| 12 | 3.67 | 0.73 | 1.84 | SRH | CZD |
| 13 | 2.92 | 0.58 | 1.46 | VNS | DKR |

From the above it is apparent that many charts within the scope of the invention may be obtained by varying the parameters mentioned. The preferred embodiment of the invention has the following characteristics. The logarithm of the size of the optotypes reduces from line to line in even. steps of 0.1. The chart has three optotypes per line. The optotypes are selected from the Sloan set. The chart has 14 lines with the top line being of the size 1.0 logMAR. As has been stated the absolute size of the optotypes is dependent on the intended viewing distance. The chart has crowding bars to all sides with the preferred spacings and widths mentioned above and having all the linking sections mentioned above.

Experiment has shown that a chart with these characteristics allows an acuity test to be made much faster than either by using the Snellen chart or the ETDRS logMAR chart, the median time for the preferred embodiment being measured at 59 seconds compared to 110 seconds for the Snellen chart.

The preferred embodiment also produced acuity measurements that were more precise and hence more reliable than those produced by a Snellen chart. 95% confidence limits of agreement for two tests of the same subject (also known as test retest reliability) obtained were: Snellen +/−0.33 logMAR, the preferred embodiment +/−0.24 logMAR, ETDRS +/−0.18 logMAR.

The preferred embodiment is therefore not only quicker to use but than the Snellen chart but, surprisingly since it has fewer letters per line, is more precise than the Snellen chart. It is therefore an ideal replacement for the Snellen chart in general clinical practice. The preferred embodiment has fewer letters on each line than does the ETDRS chart which remains preferable for research where higher precision is required. Since it has fewer letters per line than the ETDRS chart the chart of the present invention is termed herein as the "reduced" logMAR chart.

The performance of reduced logMAR charts with four and two optotypes per line and also with different size increments per line have been measured and are also within the scope of the present invention. The preferred form of chart for two and four optotypes is exactly as illustrated in FIGS. 1 and 2 with a decrement of 0.1 in the logarithm of the optotype size form one line to the next and with crowding bars, except of course that each line has two optotypes in one form of the chart and four optotypes in another form of the chart.

A chart having two optotypes per line proved to give poorer repeatability than the preferred embodiment of three per line did not result in a significantly quicker test. A chart having four per line resulted in a longer test than the preferred embodiment. A chart having three optotypes per line and having a decrement in the logarithm of the size optotypes of 0.15 instead of the preferred of 0.1 provided poorer repeatability but took roughly the same time to complete a test. Therefore the preferred embodiment of three optotypes per line and an a decrement of in the logarithm of the size of the optotypes of 0.1 from line to line is thought to give the best compromise between repeatability and speed, Of course, it is within the scope of the invention to have a chart that has some lines with more letters than others. For example, a chart could have the lines of the larger optotypes near the top having two optotypes, lines in the middle having three optotypes and lines of the smaller optotypes near the bottom having four optotypes.

Generally the charts will be produced on paper for viewing with incident light or mounted on a light box. They may also be produced as an image on a screen such as a computer monitor or may be projected.

What is claimed is:

1. A visual acuity chart having a plurality of lines of optotypes, wherein the ratio of the size of optotypes of each line of the plurality to the size of the optotypes of the preceding line is a constant, wherein the number of optotypes on each line of the plurality is three, and wherein said ratio is such that the difference between the logarithm to base 10 of the size of the optotypes of each line of the plurality and logarithm to base 10 of the size of the optotypes of each line of the plurality and the logarithm to base 10 of the size of those of the next is 0.1.

2. A visual acuity chart as claimed in claim 1 wherein each line of the plurality has three optotypes.

3. A visual acuity chart as claimed in claim 1 wherein each line of the plurality has four optotypes.

4. A visual acuity chart as claimed in claim 1 wherein each line of the plurality has two optotypes.

5. A visual acuity chart as claimed in claim 1 wherein the said optotypes are drawn from the Sloan set.

6. A visual acuity chart as claimed in claim 1 having at least one crowding bar spaced from the end of one of the said lines of optotypes or spaced above the top line of optotypes or below the bottom line of optotypes.

7. A visual acuity chart as claimed in claim 6 having two such crowding bars joined by linking sections.

8. A visual acuity chart as claimed in claim 6 wherein said crowding bar is spaced from the end of a row by half the width of the optotypes of that row.

9. A visual acuity chart as claimed in claim 6 wherein said crowding bar is spaced above the top line of optotypes or below the bottom line of optotypes by half the height of the optotypes of the top or bottom row respectively.

10. A visual acuity chart as claimed in claim 6 wherein the breadth of the crowding bar is equal to the width of the strokes of the optotypes.

11. A visual acuity chart as claimed in claim 6 wherein the said optotypes are drawn from the Sloan set.

12. A visual acuity chart having a plurality of optotypes, the size of the optotypes of the lines of the plurality decreasing line by line, said acuity chart having at least two crowding bars spaced from the ends of one of said lines of optotypes, said two crowding bars being joined by a linking section at an angle to a line perpendicular to the lines of optotypes.

13. A visual acuity chart as claimed in claim 12 having a crowding bar spaced above the top line of optotypes or below the bottom line of optotypes.

14. A visual acuity chart as claimed in claim 12 wherein said crowding bar is spaced from the end of a row by half the width of the optotypes of that row.

15. A visual acuity chart as claimed in claim 12 wherein each said crowding bar is spaced above the top line of optotypes or below the bottom line of optotypes by half the height of the optotypes of the top or bottom row respectively.

16. A visual acuity chart as claimed in claim 12 wherein the breadth of the crowding bar is equal to the width of the strokes of the optotypes.

17. A method of testing a subject's visual acuity comprising the subject viewing a visual acuity chart according to claim 1 and the subject responding by indicating his or her identification of at least a particular one of the optotypes displayed on the chart.

18. A method of testing a subject's visual acuity comprising the subject viewing a visual acuity chart according to claim 12 and the subject responding by indicating his or her identification of at least a particular one of the optotypes displayed on the chart.

19. Apparatus for producing an image, viewable by a subject, of a chart according to claim 1.

20. Apparatus for producing an image, viewable by a subject, of a chart according to claim 12.

* * * * *